(12) United States Patent
Hacker et al.

(10) Patent No.: US 7,706,853 B2
(45) Date of Patent: Apr. 27, 2010

(54) NEAR INFRARED SPECTROSCOPY DEVICE WITH REUSABLE PORTION

(75) Inventors: Thomas G. Hacker, Anaheim, CA (US); Brent William Allen, Rancho Santa Margarita, CA (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 1116 days.

(21) Appl. No.: 11/349,477

(22) Filed: Feb. 7, 2006

(65) Prior Publication Data

US 2006/0189860 A1    Aug. 24, 2006

Related U.S. Application Data

(60) Provisional application No. 60/651,886, filed on Feb. 10, 2005.

(51) Int. Cl.
*A61B 5/1455* (2006.01)
(52) U.S. Cl. ..................... 600/344; 600/323
(58) Field of Classification Search ............... 600/310, 600/340, 344, 473, 476, 322, 323
See application file for complete search history.

(56) References Cited

U.S. PATENT DOCUMENTS

| | | | |
|---|---|---|---|
| 5,217,013 A | | 6/1993 | Lewis et al. |
| 5,584,296 A | | 12/1996 | Cui et al. |
| 5,827,182 A | * | 10/1998 | Raley et al. ............. 600/323 |
| 5,839,439 A | * | 11/1998 | Nierlich et al. ........... 600/338 |
| 5,879,373 A | * | 3/1999 | Roper et al. ............. 600/344 |
| 5,902,235 A | | 5/1999 | Lewis et al. |
| 6,014,576 A | * | 1/2000 | Raley ..................... 600/344 |

(Continued)

OTHER PUBLICATIONS

T.J. Germon, P.E. Evans, N.J. Barnett, T.T. Lewis, P. Wall, and R.J. Nelson, *Changes in tissue oxyhaemoglobin concentration measured using multichannel near infrared spectroscopy during internal carotid angiography*, Apr. 25, 1997, pp. 660-664.

(Continued)

*Primary Examiner*—Eric F Winakur
*Assistant Examiner*—Etsub D Berhanu
(74) *Attorney, Agent, or Firm*—Gael Diane Tisack, Esq.; MacMillan, Sobanski & Todd, LLC

(57) ABSTRACT

A NIRS sensor device for brain monitoring is small in size, provides reliable attachment to a patient, blocks ambient light, is easy to use, is hygienic, and supports data integration with surgical and monitoring systems. The sensor device is coupled to a remote near infrared light source via a hybrid cable. Since the light source is remotely located, a source adapted for providing high energy, short pulses can easily be used so that there is less chance of interference by superficial non-brain tissues and less interference from ambient light. In addition, the remote location avoids changes in output of local light sources experienced in the prior art during hypothermia procedures (e.g., bandwidth shifts in LEDs as a result of lowered temperature). The higher energy may be achieved by the use of laser diodes as opposed to locally-mounted LEDs typically used in the prior art. The sensor device is a two-piece design comprising a reusable portion containing the photodetector(s) and a disposable portion that receives the light from the reusable portion and bends it to direct the light into the brain.

16 Claims, 9 Drawing Sheets

U.S. PATENT DOCUMENTS

| | | | | |
|---|---|---|---|---|
| 6,095,974 | A * | 8/2000 | Shemwell et al. | 600/310 |
| 6,256,523 | B1 * | 7/2001 | Diab et al. | 600/323 |
| 6,353,226 | B1 * | 3/2002 | Khalil et al. | 250/341.8 |
| 6,456,862 | B2 | 9/2002 | Benni | |
| 6,470,199 | B1 * | 10/2002 | Kopotic et al. | 600/344 |
| 6,615,065 | B1 | 9/2003 | Barrett et al. | |
| 6,678,543 | B2 * | 1/2004 | Diab et al. | 600/323 |
| 7,225,006 | B2 * | 5/2007 | Al-Ali et al. | 600/344 |
| 2002/0016536 | A1 | 2/2002 | Benni | |
| 2002/0082489 | A1 * | 6/2002 | Casciani et al. | 600/338 |
| 2002/0165440 | A1 * | 11/2002 | Mason et al. | 600/344 |
| 2004/0024297 | A1 | 2/2004 | Chen et al. | |

OTHER PUBLICATIONS

Yoko Hoshi, et al., *Interpretation of Near-Infrared Spectroscopy Signals: A Study with a newly developed perfused rat brain mode*, 2001, pp. 1657-1662.

Francesco Fabbri et al., *Bilateral near-infrared monitoring of the cerebral concentration and oxygen-saturation of hemoglobin during right unilateral electro-convulsive therapy*, 2003, pp. 193-204.

Marie-Christine Taillefer, PhD., André Y. Denault, MD FRCPC, *Cardiothoracic Anesthesia, Respiration and Airway*, 2005, pp. 79-87.

* cited by examiner

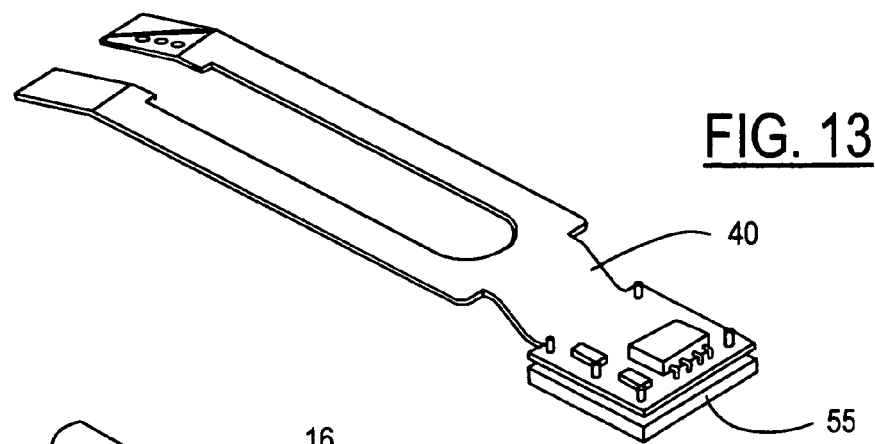
FIG. 13
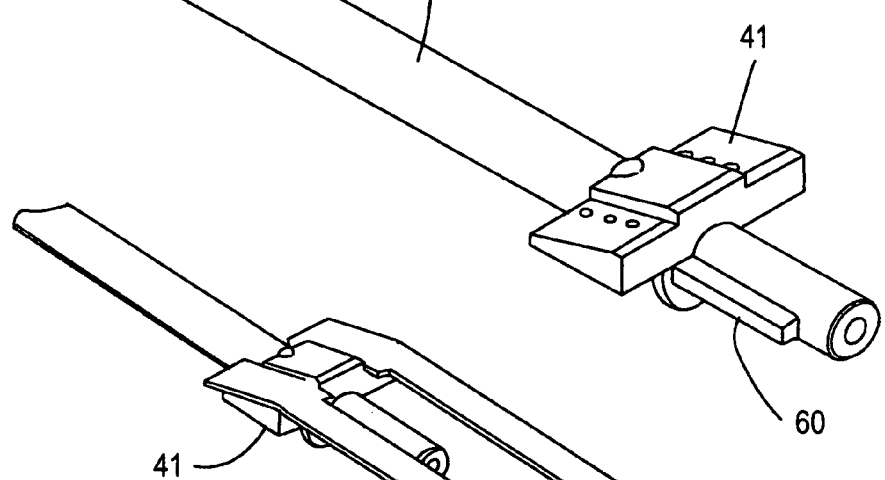
FIG. 14
FIG. 15
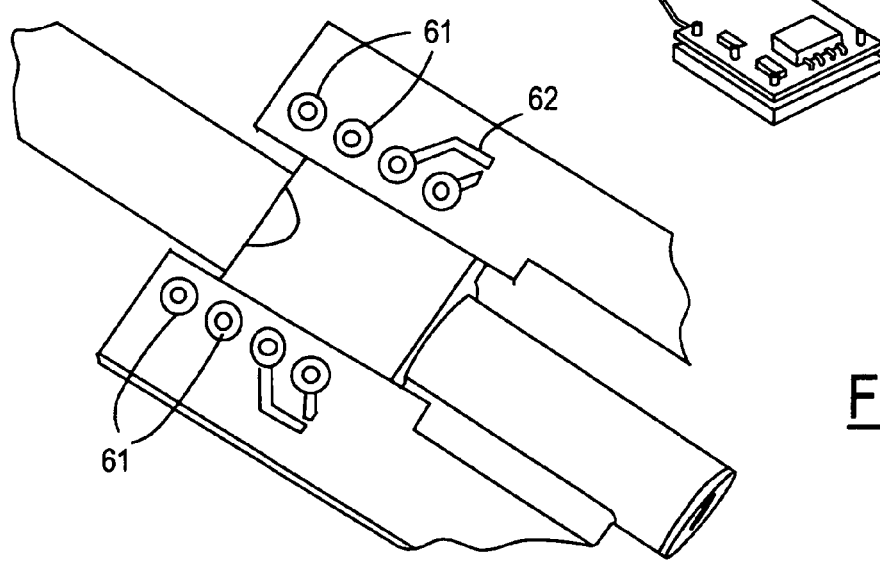
FIG. 16

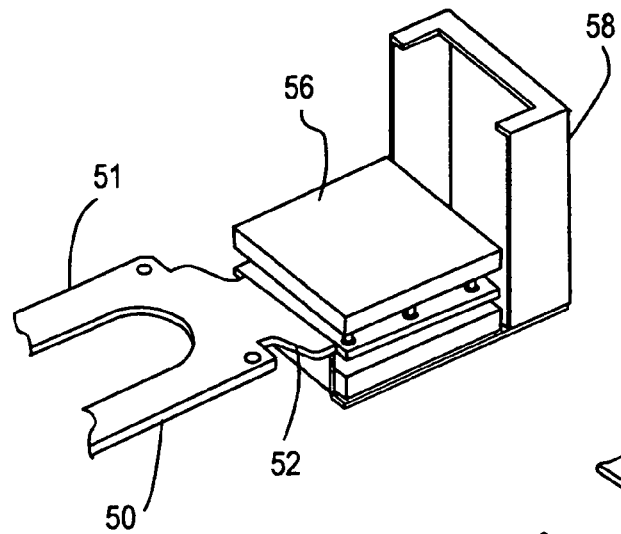
FIG. 17
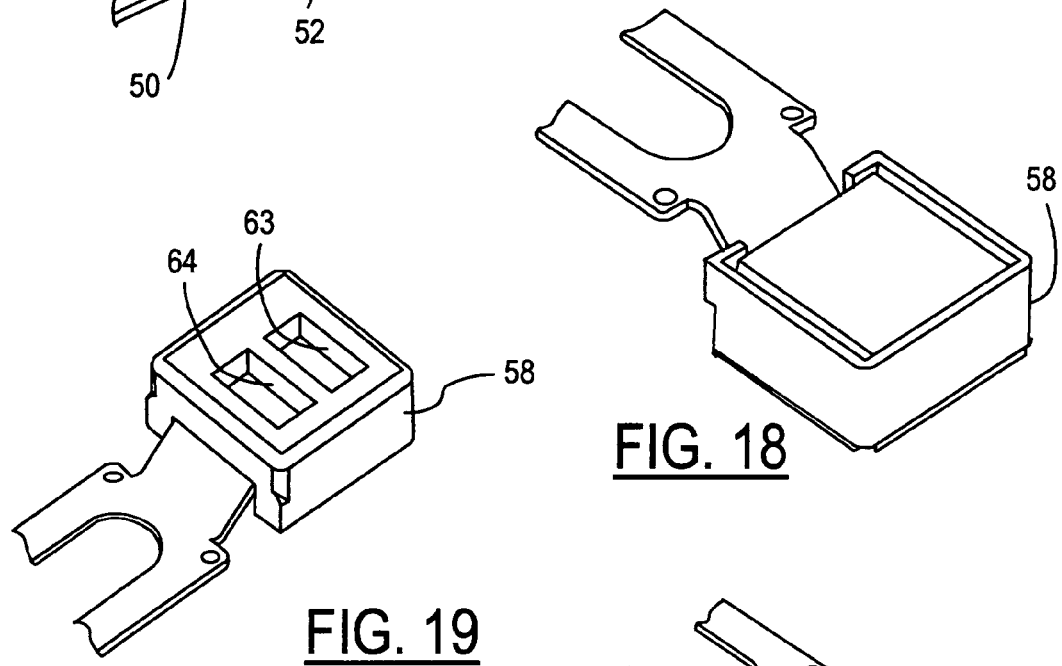
FIG. 18
FIG. 19
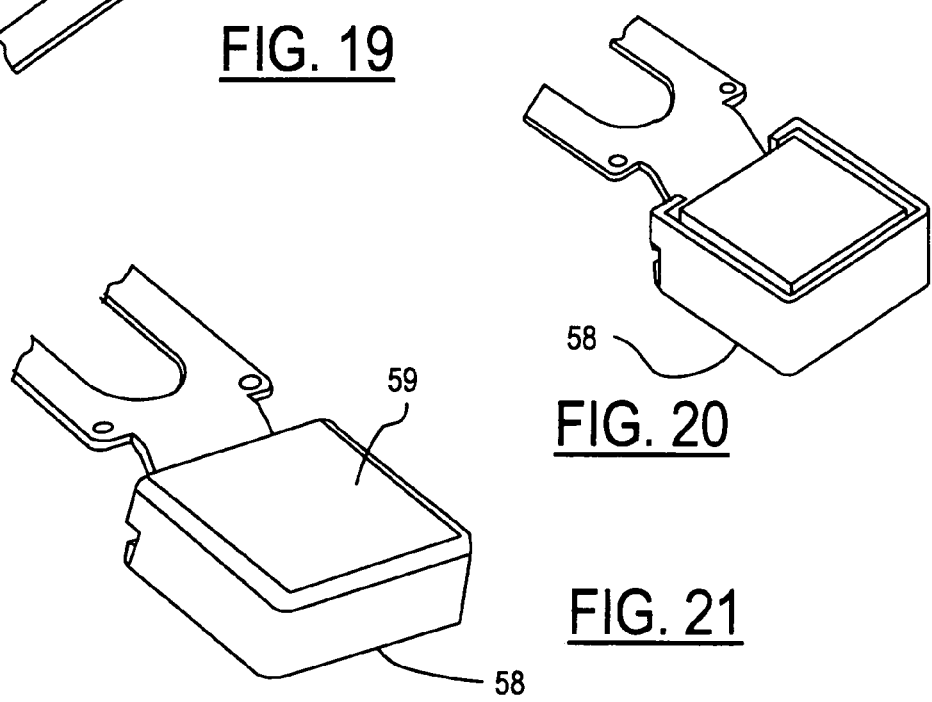
FIG. 20
FIG. 21

NEAR INFRARED SPECTROSCOPY DEVICE WITH REUSABLE PORTION

CROSS REFERENCE TO RELATED APPLICATIONS

This application claims priority to provisional U.S. application Ser. No. 60/651,886, filed Feb. 10, 2005.

STATEMENT REGARDING FEDERALLY SPONSORED RESEARCH

Not Applicable.

BACKGROUND OF THE INVENTION

The present invention relates in general to measurement of oxygenation-related parameters of a patient during surgery, and, more specifically, to a near infrared spectroscopy sensor device having reusable and disposable portions and specially adapted for monitoring hemoglobin level and/or oxygen carrying capacity of blood in the brain during cardiac surgery.

During cardiac surgery, it is very useful for surgeons to monitor oxygenation-related parameters within the brain. Major causes of neurological damage during cardiac surgery include decreased cerebral blood flow, insufficient oxygenation, insufficient hemoglobin concentration, and cerebral embolism. When the brain experiences low oxygen levels during surgery, there is increased risk of neurological problems after surgery which often results in a greater need for critical care and longer hospital stays. Use of brain monitoring devices can help members of the surgical team monitor changes in the oxygen level and/or hemoglobin concentration of the brain and take action before brain damage occurs.

Some previous methods of monitoring the brain were invasive and created other medical risks. Near infrared spectroscopy (NIRS) has been developed as a noninvasive method of monitoring the oxygen level and hemoglobin concentration of blood perfusing the brain employing light emitters and sensors attached to a patient's forehead. Known systems have had unresolved problems in that current sensors are large and bulky and can be affected by exterior light sources. The sensors also have difficulty staying attached to the forehead. Smaller sensors are needed that not only stay firmly attached to the forehead, but leave room on the forehead for other monitors, such as a BIS monitor for anesthesia monitoring. Thus, there is a need in the art for a small NIRS sensor device that stays firmly attached to the patient's forehead and is less affected by outside light.

There exist further unmet needs to ensure safe, hygienic use of NIRS sensors from the standpoint of the patient and to improve efficiency, ease of use, and ease of integration with other surgical/monitoring systems from the standpoint of the medical practitioner.

SUMMARY OF THE INVENTION

The present invention is an improved NIRS sensor device for brain monitoring that is small in size, provides reliable attachment to a patient, blocks ambient light, is easy to use, is hygienic, and supports data integration with surgical and monitoring systems. The sensor device is coupled to a remote near infrared light source via a hybrid cable. Since the light source is remotely located, a source adapted for providing high energy, short pulses can easily be used so that there is less chance of interference by superficial non-brain tissues and less interference from ambient light. In addition, the remote location avoids changes in output of local light sources experienced in the prior art during hypothermia procedures (e.g., bandwidth shifts in LEDs as a result of lowered temperature). The higher energy may be achieved by the use of laser diodes as opposed to locally-mounted LEDs typically used in the prior art. The sensor device is a two-piece design comprising a reusable portion containing the photodetector (s) and a disposable portion that receives the light from the reusable portion and bends it to direct the light into the brain. The disposable portion is the only portion that is adhered to the patient's forehead. The cable is preferably a hybrid type that contains both optical and electrical conductors and is optically and electromagnetically isolated. By virtue of the design, the entire assembly is easily manufactured, and its use is more manageable for the end user since only one cable is required.

In one aspect of the invention, a near infrared spectroscopy system monitors an oxygenation-related parameter beneath a body surface of a patient. A reusable probe portion comprises a ferrule member mounted to a hybrid cable for conveying near infrared light from a remote source. The reusable probe portion further comprises a pair of photodetectors. The ferrule member has a termination spaced from the pair of photodetectors. A disposable coupler portion comprises a flexible housing fixedly mounting a light channel member adapted to be selectively coupled to the termination of the ferrule member for directing the near infrared light toward the body surface. The flexible housing further comprises an adhesive layer for temporarily attaching the disposable coupler portion to the body surface. The flexible housing includes a window disposed in alignment with the pair of infrared detectors for admitting reflected near infrared light from the patient when the disposable coupler portion is releasably connected with the reusable probe portion.

BRIEF DESCRIPTION OF THE DRAWINGS

FIG. 13 is a perspective view of photodetectors mounted to a flexible circuit board of the reusable portion.

FIG. 14 shows a ferrule member mounted to the hybrid cable.

FIGS. 15 and 16 show the interconnection of the flexible circuit board with the ferrule member.

FIGS. 17-21 show an EMI shield and plastic housing for containing the photodetectors.

DETAILED DESCRIPTION OF PREFERRED EMBODIMENTS

Figure 1:
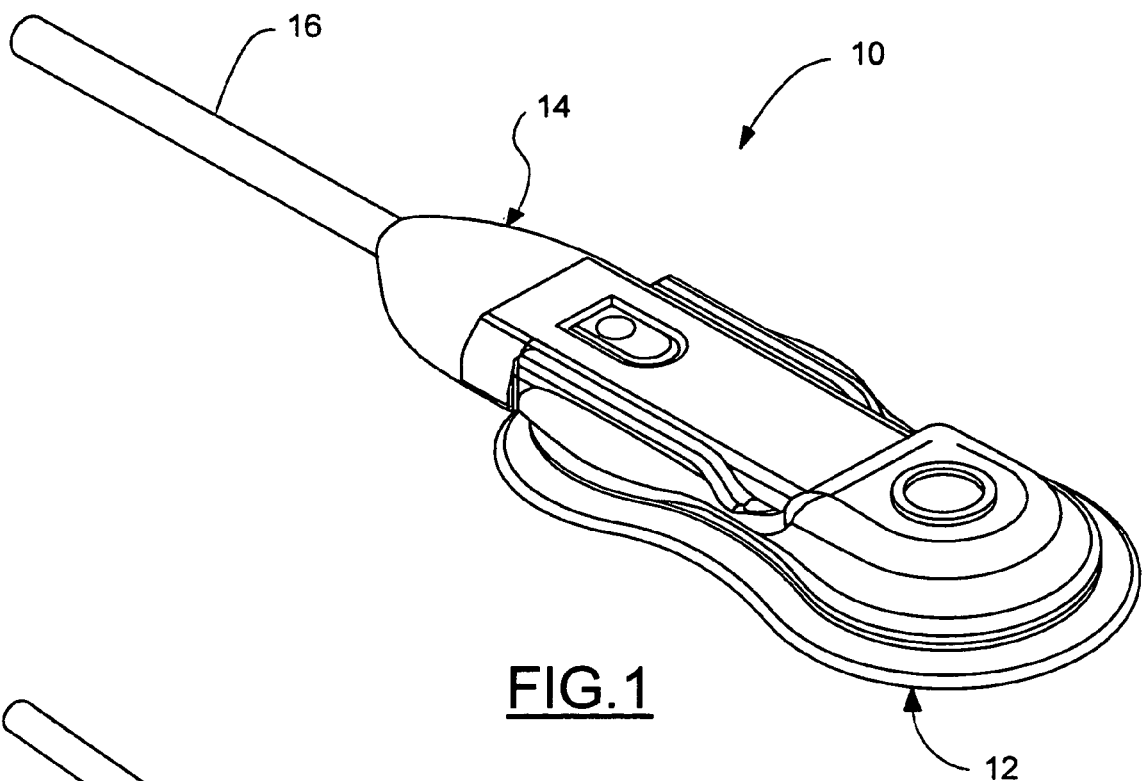
FIG. 1 is an isometric view of a fully assembled NIRS sensor including a reusable portion mated with a disposable portion.
Figure 2:
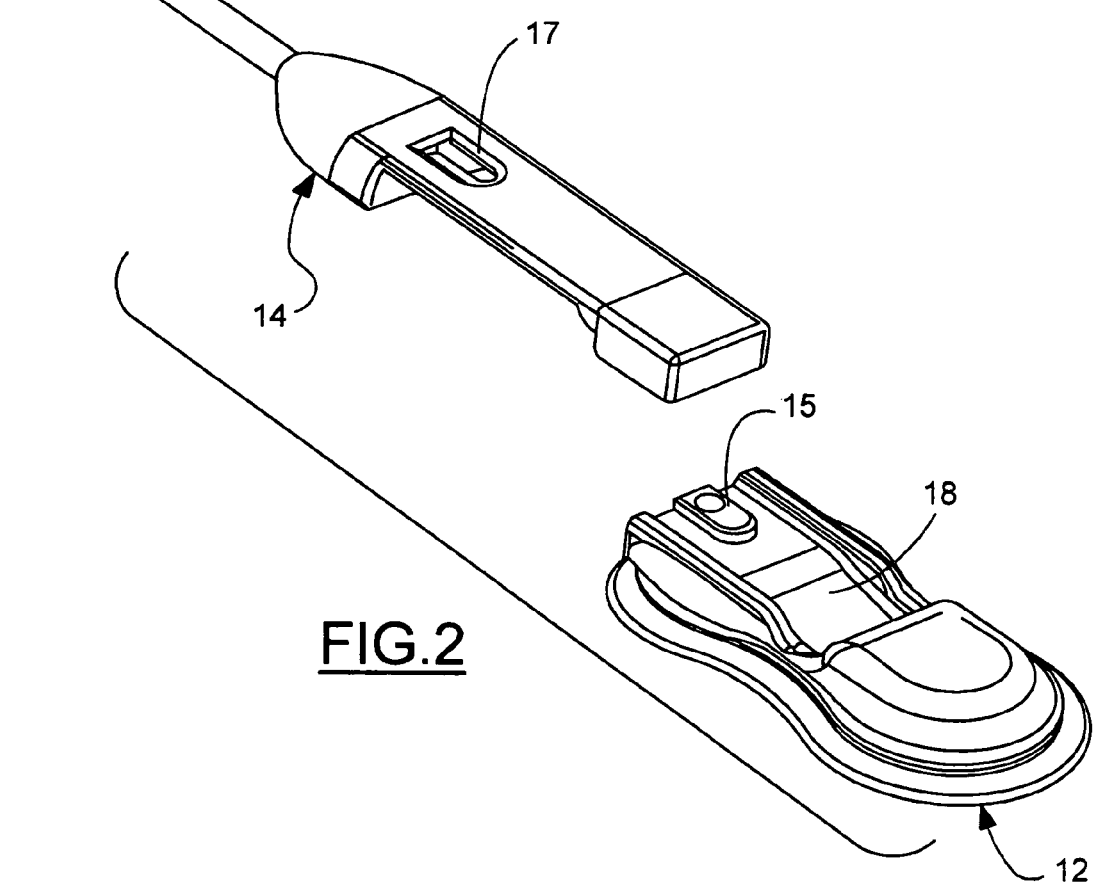
FIG. 2 is an isometric view of the reusable and disposable portions prior to mating.

Referring now to FIGS. 1 and 2, a NIRS sensor device 10 comprises a disposable coupler portion 12 and a reusable probe portion 14. A hybrid (optical/electrical) cable 16 integrated into reusable portion 14 provides optical and electrical connection to a monitor controller (not shown). Reusable portion 14 can be releasably inserted within a receiving slot 18 of disposable portion 12. Locking features 15 and 17 interlock when the two portions are mated to help keep them together. Feature 15 is part of a soft rubber overmold and is easily compressed within feature 17. Moreover, it can be selectively released when it is desired to unmate the two portions.

Figure 3:
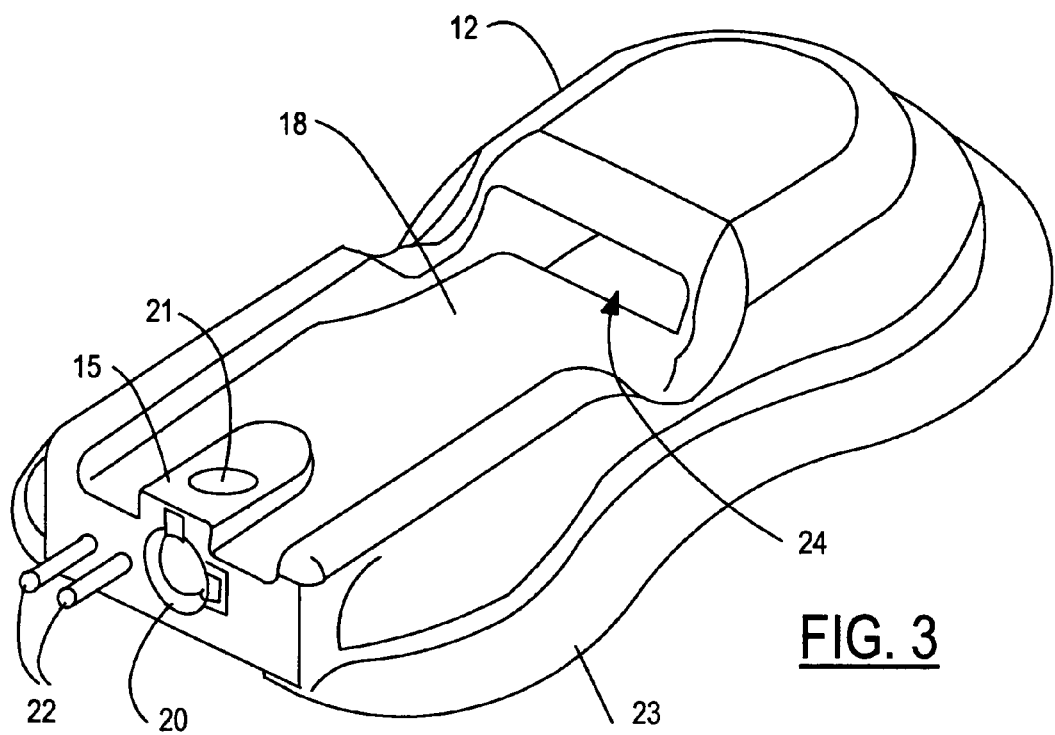
FIG. 3 is an isometric view showing the rear side of the disposable portion.

As shown in FIG. 3, a light channel member 20 including an indicator lens 21 and pin members 22 is embedded in an overmold 23 that defines receiving slot 18 and a window 24 that receives the photodetector end of reusable probe portion 14. Lens 21 is centrally located in feature 15 so that it is visible after the mating of portions 12 and 14.

Figure 4:
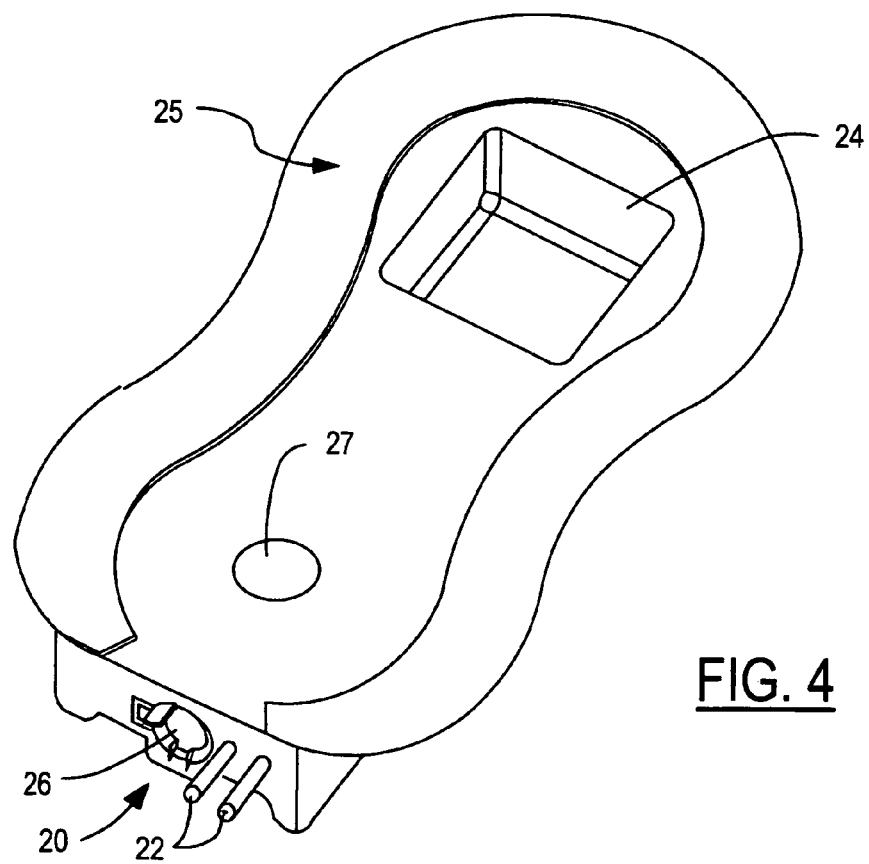
FIG. 4 is an isometric view showing the bottom, patient contacting side of the disposable portion.

FIG. 4 shows a bottom, patient-contacting surface 25 of disposable coupler portion 12 which includes an adhesive layer for attaching the device to a patient's forehead. Overmold 23 is pliable so that it can accommodate the contours of the forehead or other attachment site. Any conventional biocompatible adhesive may be used as is known in the art. Light channel member 20 includes an input coupler 26 for receiving near infrared light from reusable portion 14 and an exit 27 for directing the near infrared light perpendicularly toward the body (e.g., skin) surface of the patient.

Figure 5:
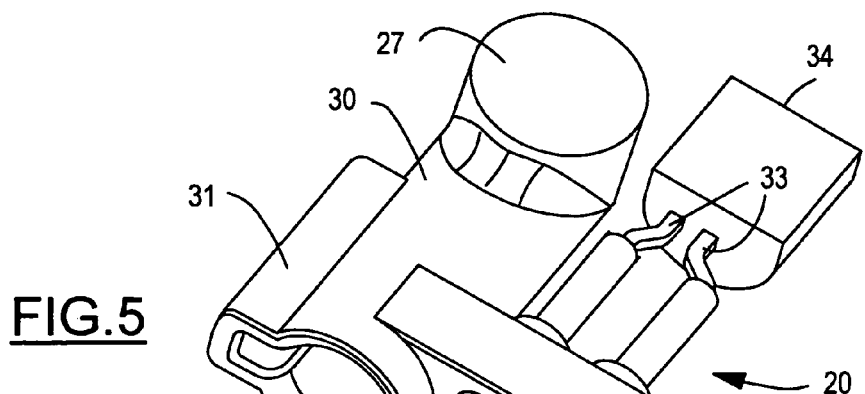
FIG. 5 is a bottom perspective view of one embodiment of a light channel member and electronic memory of the disposable portion.

The bottom side of channel member 20 is shown in greater detail in FIG. 5. Light channel 30 extends between input coupler 26 and exit 27 and has a keying slot 31 for receiving a corresponding tab on the hybrid cable. A flange 32 includes holes for receiving tubular pin members 22 which may be swaged in place. Connecting pins 33 of an electronic memory device 34 are electrically mounted (e.g., by press fit) within pin members 22 for external connection. Light channel member 20 further includes a light guide 35 for receiving visible light from a device within reusable probe portion 14 and providing it to indicator lens 21.

Figure 6:
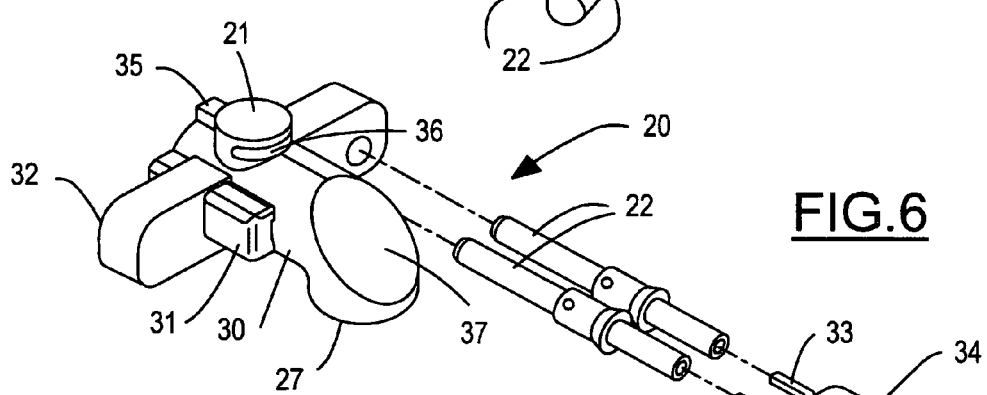
FIG. 6 is an exploded perspective view of another embodiment of the light channel member.
Figure 7:
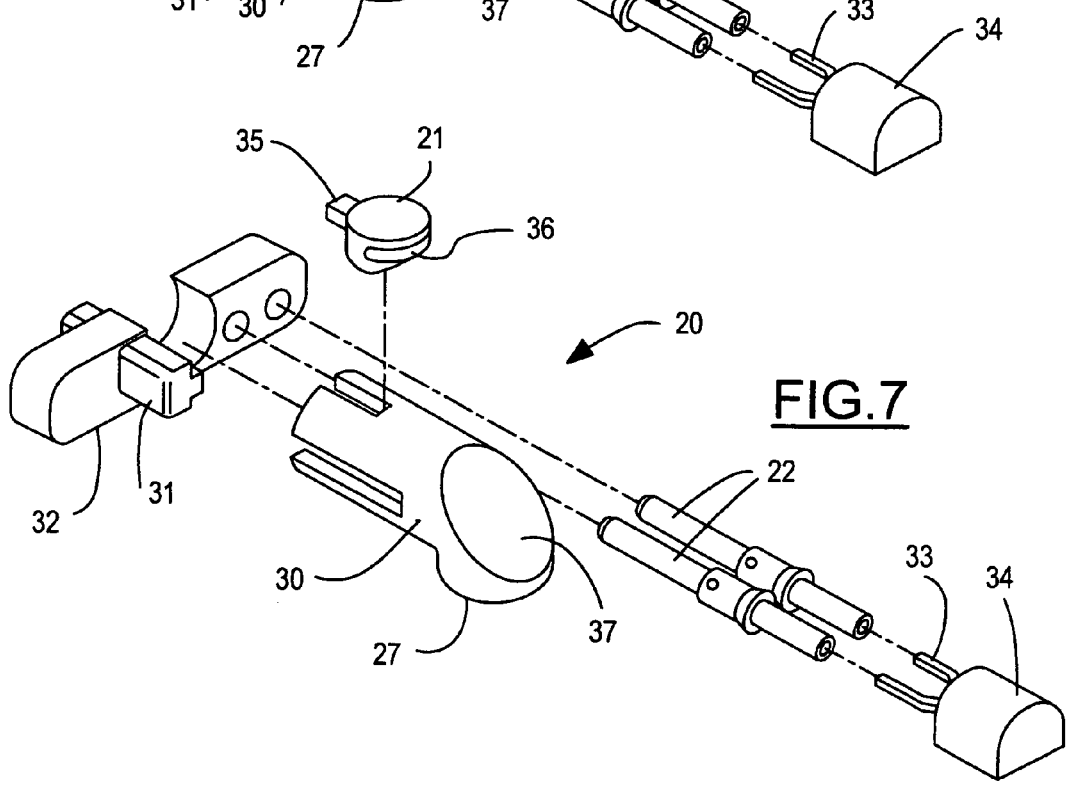
FIG. 7 is an exploded perspective view of the embodiment of FIG. 6.
Figure 8:
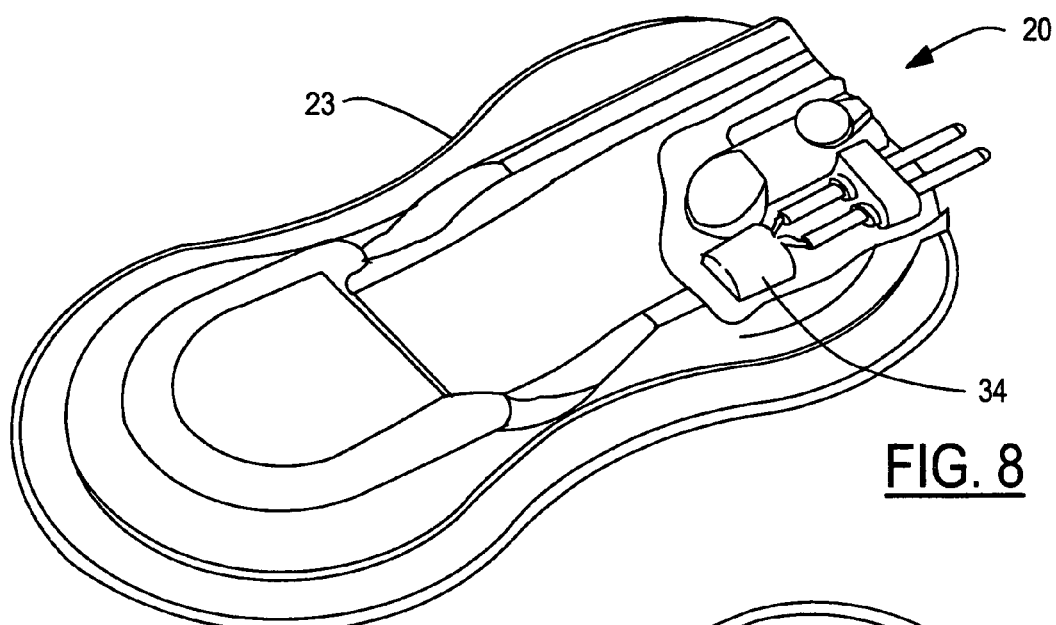
FIG. 8 is a partially broken-away view showing the flexible housing overmolded on the light channel member.
Figure 9:
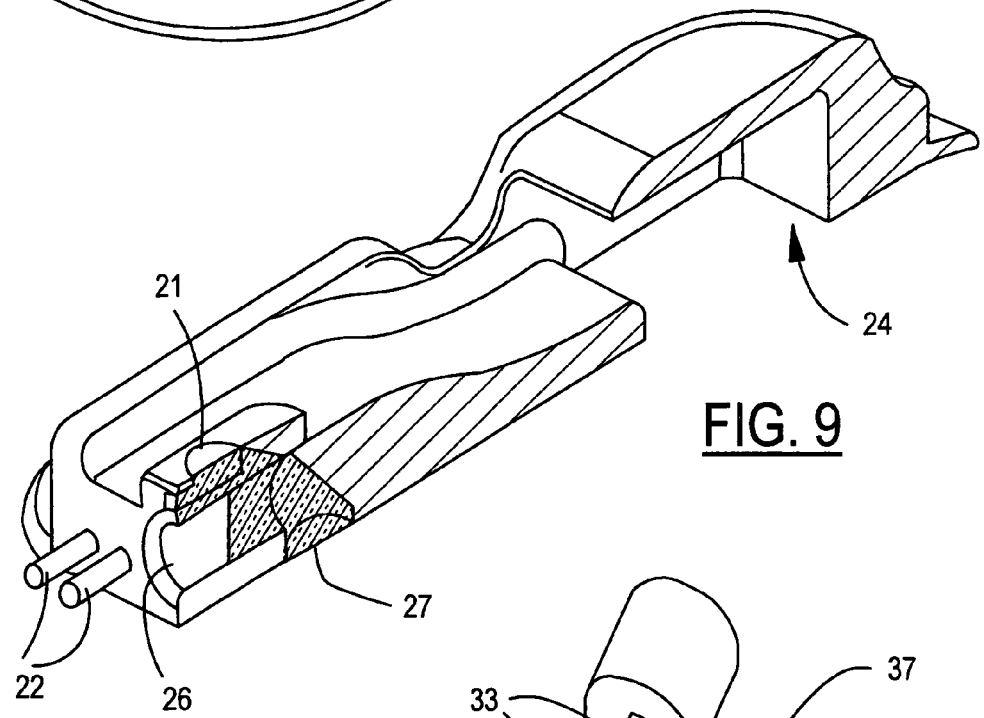
FIG. 9 is a perspective, cross-sectional view of the disposable portion.
Figure 10:
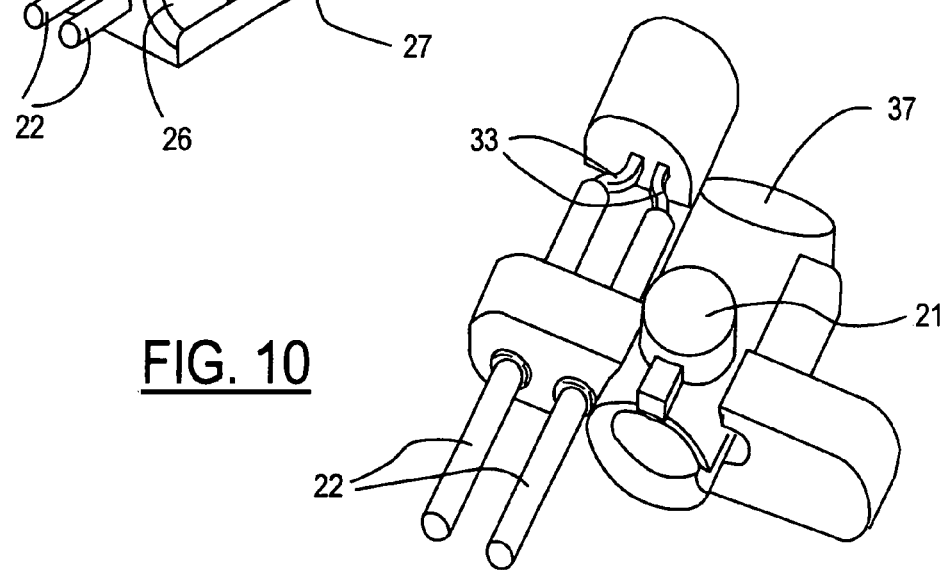
FIG. 10 is yet another view of the light channel member.

A top perspective view of a slightly modified embodiment of channel member 20 is shown in FIGS. 6 and 7. This embodiment differs in that flange 32 extends from both sides of channel 30. In this view, the coupling of visible light through light guide 35 toward indicator lens 21 can be seen. An angled, reflective surface 36 below lens 21 helps direct the indicating light upward for easy viewing by a user. An angled, reflective surface 37 is also formed within channel 30 to bend the near infrared light by 90° to enter the patient perpendicularly while allowing the cable providing the near infrared light to lie parallel to body surface of the patient. FIG. 8 shows light channel member 20 including electronic memory 34 encapsulated within the soft rubber overmold 23. FIG. 9 shows a cross section of the encapsulated parts. FIG. 10 shows how connection pins 33 may be press fit into tubular pin members 22 prior to encapsulation.

Figure 11:
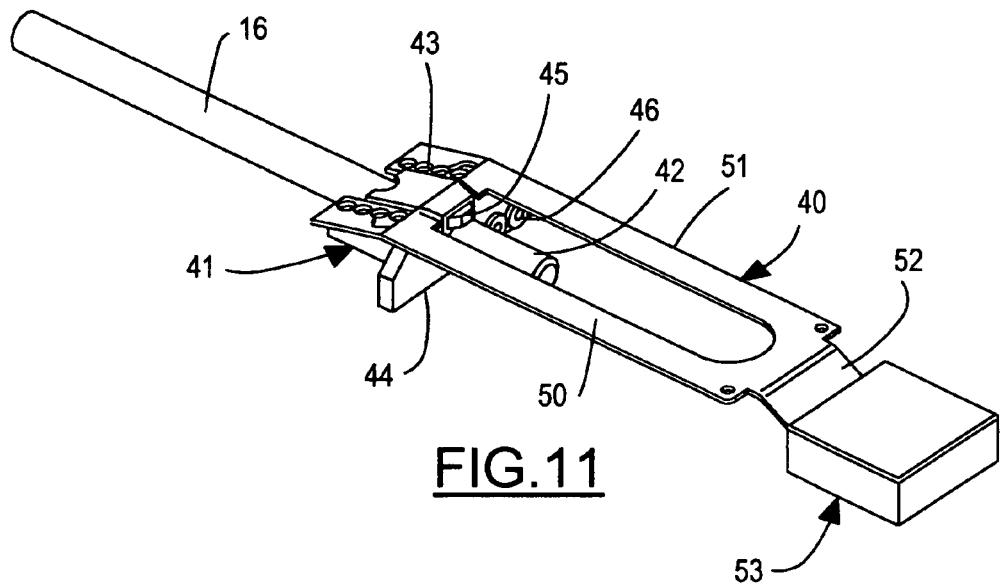
FIG. 11 is a perspective view of the reusable portion with its overmold removed.

Turning now to the detailed construction of the preferred embodiment for reusable probe portion 14, FIG. 11 shows a flexible printed circuit board 40 connected to a ferrule member 41 which is mounted near the end of hybrid cable 16. An optical guide 42 delivers near infrared light from a remote source (e.g., located at a monitor controller or device bay). Electrical conductors within cable 16 are broken out and routed through ferrule member 41 to a plurality of connection points 43 on flexible circuit board 40. A rigid circuit board 44 is mounted to an end face of ferrule member 41 and is also connected to electrical conductors from cable 16. Board 44 includes a light generator 45 (preferably and LED) for providing visible light to light guide 35 in the light channel member of the disposable coupler portion when power is received via cable 16. Receptacles 46 receive pin members 22 when the two device portions are mated so that circuits within the monitor controller can communicate with electronic memory 34.

Figure 12:
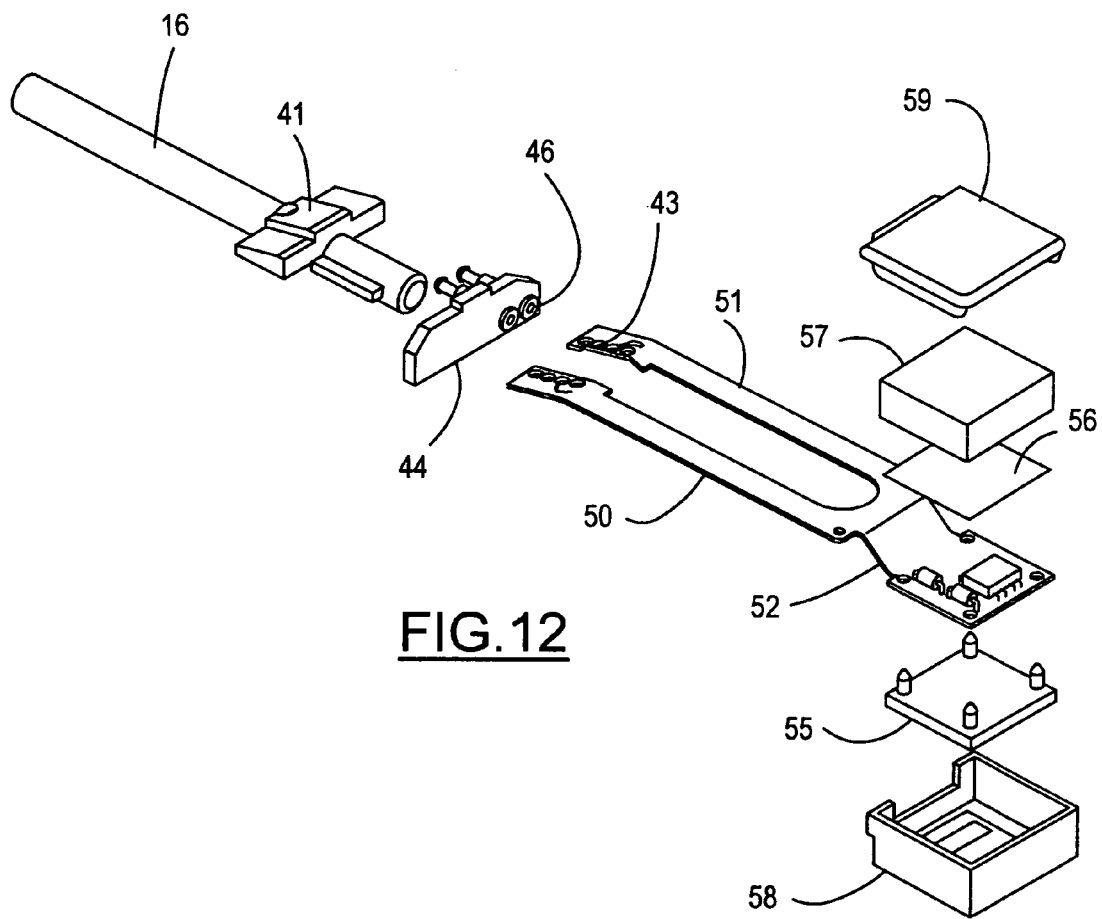
FIG. 12 is an exploded, perspective view of the reusable portion of FIG. 11.

Flexible circuit board 40 includes two elongated finger sections 50 and 51 extending to a distal end 52 where board 40 connects to a photodetector assembly 53. As shown in exploded view in FIG. 12, distal end 52 may have interface circuit components mounted thereon. A photodetector integrated circuit device 55 is connected to distal board end 52, e.g., by soldering. An insulating foam piece 56 overlies the components on distal board end 52 and insulates them from an EMI cover or shield 57. A plastic housing having a lower cup 58 and a lid 59 is attached to seal photodetector assembly 53.

FIGS. 13-21 illustrate several representative steps in a preferred fabrication process for the reusable probe portion. In FIG. 13, all components including the photodetector unit 55 are soldered to flexible board 40. In FIG. 14, ferrule member 41 is installed onto the end of hybrid cable 16 which has been prepared by stripping the electrically conductive wires and exposing the optical guide. The wires may be routed through passages within ferrule member 41 for soldering to the circuit boards. A keying feature 60 is shown integral with ferrule member 41 for mating with keying slot 31 of the light channel member. Ferrule 41 may preferably be adhesively bonded onto cable 16. FIGS. 15 and 16 show the assembly of flexible board 40 to ferrule member 41 in greater detail. Conductive wires from cable 16 are soldered to holes 61 in board 40. Signals are then able to be conducted via traces 62 to and from the photodetector assembly.

As shown in FIGS. 17-21, insulator 56 is placed over distal end 52 of board 40. In FIG. 18, the photodetector assembly is inserted into the lower cup 58. As shown in FIG. 19, the bottom of cup 58 includes apertures 63 and 64 corresponding to the locations of a pair of photodetector elements as used in known NIRS sensing. A silicon sealer is preferably injected within cup 58 around the photodetector assembly and around apertures 63 and 64 to make the reusable probe portion watertight. In FIG. 20, the insulator and EMI cover have been inserted into cup 58. FIG. 21 shows the photodetector assembly after lid 59 is atached to cup 58.

The central section of flexible board 40 is covered by a further plastic housing or an overmold to protect the circuit traces and to provide durability.

Figure 22:
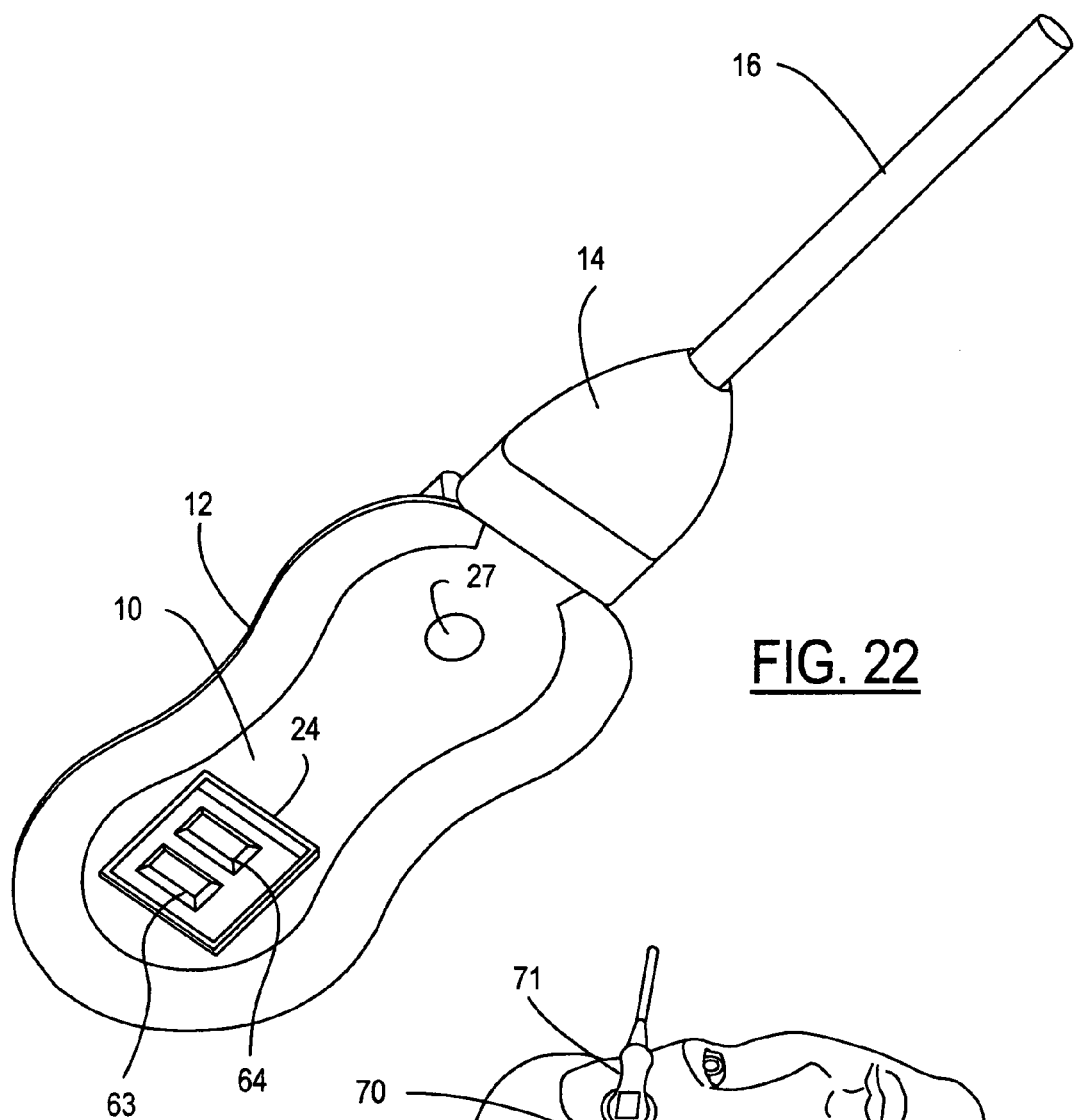
FIG. 22 is a bottom, isometric view of the assembled NIRS sensor device.

FIG. 22 shows a bottom perspective view of the two portions in a mated condition. After mating, the photodetectors are in alignment with window 24 in disposable portion 12. Furthermore, the two photodetectors which receive reflected light from the patient through apertures 63 and 64 are spaced at predetermined distances from exit 27 of light channel 30 in accordance with the known operation of NIRS sensors.

Figure 23:
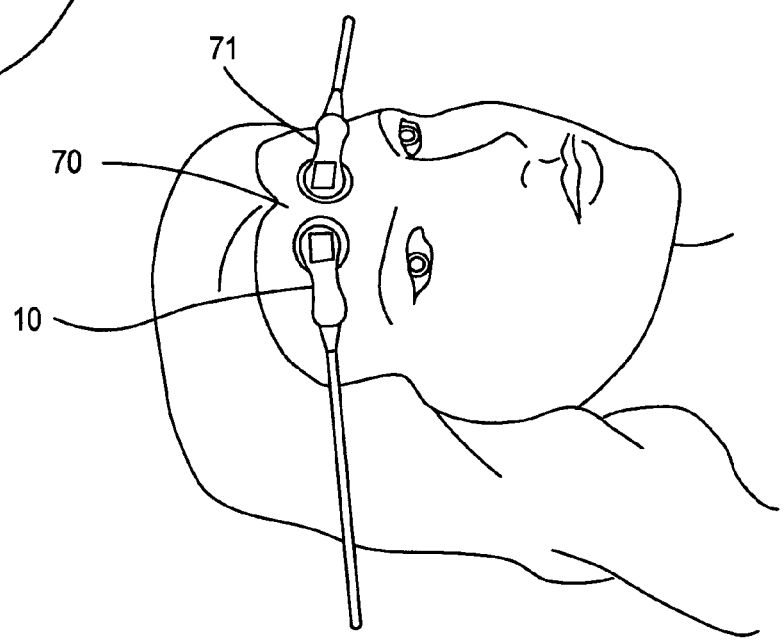
FIG. 23 shows a pair of NIRS sensors attached to a patient.

As seen in FIG. 23, NIRS device 10 is mounted to forehead 70 of a patient 71 during monitoring. For different types of monitoring, attachment to other skin surfaces in other areas of the patient's body may be employed. Device 10 is sufficiently compact that other sensors for monitoring other parameters such as a sensor 71 may also be mounted to the forehead.

Figure 24:
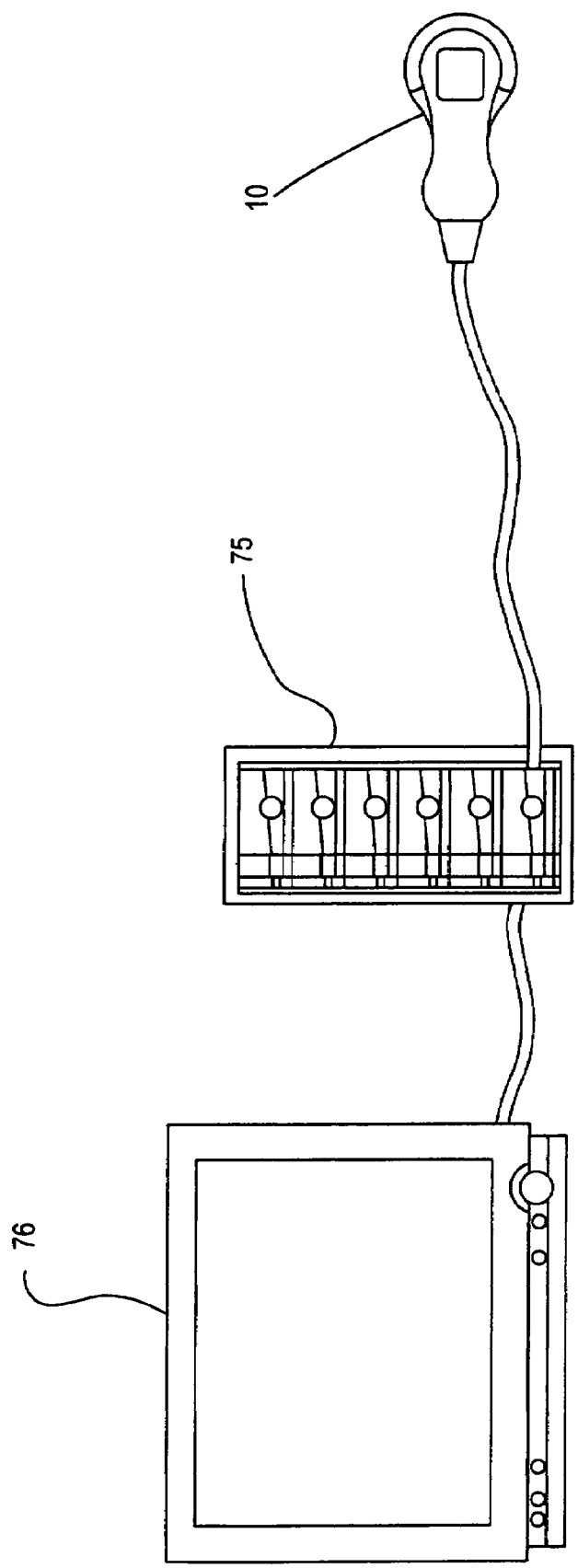
FIG. 24 shows a monitoring system including a monitor controller.

FIG. 24 shows an overall monitoring system wherein device 10 is connected to a monitor controller or device bay 75 which preferably includes programmable computing elements. A monitor 76 displays the measured oxygenation-related parameters for viewing by the medical practitioners.

What is claimed is:

1. A near infrared spectroscopy system for monitoring an oxygenation-related parameter beneath a body surface of a patient, comprising:
   a reusable probe portion comprising a ferrule member mounted to a hybrid cable for conveying near infrared light from a remote source, said reusable probe portion further comprising a pair of photodetectors, said ferrule member having a termination spaced from said pair of photodetectors; and
   a disposable coupler portion comprising a flexible housing with a receiving slot into which said reusable probe portion is releasably inserted, wherein said disposable coupler portion further comprises a light channel member adapted to be selectively coupled to said termination of said ferrule member for directing said near infrared light toward said body surface, wherein said flexible housing further comprises an adhesive layer for temporarily attaching said disposable coupler portion to said body surface, and wherein said flexible housing includes a window disposed in alignment with said pair of infrared detectors for admitting reflected near infrared light from said patient when said disposable coupler portion is releasably connected with said reusable probe portion, whereby only said disposable coupler portion is configured to adhere to said body surface.

2. The system of claim 1 wherein said light channel member comprises a light bender having a reflective surface for directing said near infrared light in a direction substantially perpendicular to said body surface.

3. The system of claim 2 wherein said flexible housing comprises a substantially opaque overmold including soft rubber.

4. The system of claim 1 wherein said reusable probe portion further comprises:
   an elongated flexible printed circuit board mounted to said ferrule member at a first end and connected to said pair of photodetectors at a second end, wherein said flexible printed circuit board includes conductive traces for interconnecting said photodetectors to said hybrid cable.

5. The system of claim 4 further comprising:
   an EMI cover mounted at said second end;
   a rigid housing containing said photodetectors and said EMI cover; and
   an overmolded body covering said flexible printed circuit board.

6. The system of claim 5 wherein said overmolded body of said reusable probe portion and said flexible housing of said disposable coupler portion include respective locking features for positively retaining said disposable coupler portion and said reusable probe portion when connected for use.

7. The system of claim 6 wherein said photodetectors are respectively spaced at predetermined distances from said light channel member when connected for use.

8. A sensor device for a brain monitoring system using near infrared spectroscopy, comprising:
   a reusable portion; and
   a disposable portion;
   wherein said reusable portion comprises a ferrule member for coupling to a near infrared light source, a flexible circuit board, a photodetector mounted to said flexible circuit board at a distal end opposite said ferrule member, an EMI shield disposed around a portion of said photodetector, and an overmold that covers at least said flexible circuit board; and
   wherein said disposable portion comprises a light bending optical channel, electronic connecting pins for interfacing to said flexible circuit board, an electronic memory chip for storing data, and a flexible housing overmold having a patient contact adhesive layer and having a receiving slot into which said reusable probe portion is releasably inserted so that only said disposable coupler portion configured to adhere to a patient.

9. The sensor device of claim 8 wherein said flexible housing overmold is substantially opaque for blocking ambient light from said photodetector.

10. The sensor device of claim 8 wherein said data stored in said memory chip relates to a patient and is encrypted.

11. The sensor device of claim 8 wherein said reusable portion further comprises a hybrid cable for conveying near infrared light from a remote light source and for electrically connecting said sensor device to a monitor controller.

12. A method of measuring an oxygenation-related parameter during surgery of a patient using a monitoring system having a remote near infrared light source and a controller and using a sensor device having a reusable portion and a disposable portion, said method comprising the steps of:
   mating said reusable portion and said disposable portion to conduct near infrared light from said source through said mated portions and projecting out of an exit from said disposable portion, wherein said disposable portion includes a receiving slot into which said reusable probe portion is releasably inserted, and as a result of said mating, a photodetector in said reusable portion is disposed in a window formed in said disposable portion at a predetermined distance from said exit, said reusable portion having a ferrule member mounted to a hybrid cable for conveying near infrared light from said remote near infrared light source, and said disposable portion having a light channel member adapted to be selectively coupled to said ferrule member for directing said near infrared light out of said exit;
   attaching said disposable portion to a skin surface of said patient over an area of interest so that said reusable portion does not contact said skin surface;
   illuminating said area of interest with said near infrared light;
   detecting reflected light with said photodetector as a measure of said oxygenation-related parameter;
   removing said disposable portion from said skin surface after completion of said surgery;
   unmating said reusable portion from said disposable portion; and
   mating said reusable portion to a second disposable portion to measure an oxygenation-related parameter of a second patient during a second surgery.

13. A near infrared spectroscopy system for monitoring an oxygenation-related parameter beneath a body surface of a patient, comprising:
   a reusable probe portion comprising a ferrule member mounted to a hybrid cable for conveying near infrared light from a remote source, said reusable probe portion further comprising a pair of photodetectors, said ferrule member having a termination spaced from said pair of photodetectors; and a disposable coupler portion comprising a flexible housing with a receiving slot into which said reusable probe portion is releasably inserted, wherein said disposable coupler portion further comprises a light channel member adapted to be selectively coupled to said termination of said ferrule member for directing said near infrared light toward said body surface, wherein said flexible housing further comprises an adhesive layer for temporarily attaching said disposable coupler portion to said body surface, wherein said flexible housing includes a window disposed in alignment with said pair of infrared detectors for admitting reflected near infrared light from said patient when said disposable coupler portion is releasably connected with said reusable probe portion, wherein said disposable coupler portion further comprises an electronic memory, wherein said near infrared spectroscopy system is adapted to be coupled to a monitor controller via said hybrid cable, and wherein said reusable probe portion includes a data circuit for coupling with said electronic memory to transmit information between said electronic memory and said monitor controller via said hybrid cable.

14. The system of claim 13 wherein said electronic memory comprises an integrated circuit having connection pins and wherein said disposable coupler portion further comprises pin members mounted to said light channel member for receiving said connection pins at one end thereof and for projecting from said disposable coupler portion at the other end thereof to join with said hybrid cable.

15. The system of claim 13 wherein said information stored in said electronic memory is associated with a patient, and wherein said patient information is accessible to said monitor controller.

16. A near infrared spectroscopy system for monitoring an oxygenation-related parameter beneath a body surface of a patient, comprising:

a reusable probe portion comprising a ferrule member mounted to a hybrid cable for conveying near infrared light from a remote source, said reusable probe portion further comprising a pair of photodetectors, said ferrule member having a termination spaced from said pair of photodetectors; and a disposable coupler portion comprising a flexible housing with a receiving slot into which said reusable probe portion is releasably inserted, wherein said disposable coupler portion further comprises a light channel member adapted to be selectively coupled to said termination of said ferrule member for directing said near infrared light toward said body surface, wherein said flexible housing further comprises an adhesive layer for temporarily attaching said disposable coupler portion to said body surface, wherein said flexible housing includes a window disposed in alignment with said pair of infrared detectors for admitting reflected near infrared light from said patient when said disposable coupler portion is releasably connected with said reusable probe portion;

wherein said reusable probe portion further comprises a light generator mounted to said ferrule member for generating a visible emission when receiving electrical power from said hybrid cable; and wherein said disposable coupler portion further comprises a lens receiving said visible emission and radiating said visible emission outside said disposable coupler portion to indicate that said electrical power is being received.

* * * * *